(12) United States Patent
Banks

(10) Patent No.: US 8,425,934 B2
(45) Date of Patent: Apr. 23, 2013

(54) PHARMACEUTICAL COMPOSITIONS

(75) Inventor: Simon Banks, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 851 days.

(21) Appl. No.: 11/841,030

(22) Filed: Aug. 20, 2007

(65) Prior Publication Data

US 2008/0058353 A1    Mar. 6, 2008

Related U.S. Application Data

(60) Provisional application No. 60/823,083, filed on Aug. 21, 2006.

(51) Int. Cl.
*A61K 9/20*    (2006.01)

(52) U.S. Cl.
USPC .......................................................... 424/465

(58) Field of Classification Search ........................ None
See application file for complete search history.

(56) References Cited

U.S. PATENT DOCUMENTS

| 2003/0165563 A1* | 9/2003 | Murphy et al. ............... 424/465 |
| 2004/0001885 A1 | 1/2004 | Kositprapa et al. |

FOREIGN PATENT DOCUMENTS

| WO | 0034283 | | 6/2000 |
| WO | 01/36421 | A1 | 5/2001 |
| WO | 0192262 | | 12/2001 |
| WO | WO 01/92262 | * | 12/2001 |
| WO | 03068238 | | 8/2003 |
| WO | 2004024127 | | 3/2004 |
| WO | 2004037263 | | 5/2004 |
| WO | 2004052342 | | 6/2004 |
| WO | 2005/113006 | A2 | 12/2005 |
| WO | 2008024045 | | 2/2008 |

OTHER PUBLICATIONS

Copending U.S. Appl. No. 11/841,067, filed Aug. 20, 2007.
Office Action dated Jul. 14, 2010 received in copending U.S. Appl. No. 11/841,067.
Fitzpatrick et al., "Effect of moisture on polyvinylpyrrolidone in accelerated stability testing," Int J. Pharm. (2002) 246 (1-2):143-151.
Kiekens et al., "Effect of the storage conditions on the tensile strength of tablets in relation to the enthalpy relaxation of the binder," Pharm Res. (2000) 17(4):490-493.
Alderborn et al., "Moisture adsorption and tabletting. III. Effect on tablet strength-post compaction storage time profiles," International Journal of Pharmaceutics (1991) 73:249-258.
Gordon et al., "The effect of aging on the dissolution of wet granulated tablets containing super disintegrants," International Journal of Pharmaceutics (1993) 97:119-131.
Li et al., "The role of intra- and extragranular microcrystalline cellulose in tablet dissolution," Pharmaceutical Development and Technology (1996) 1(4):343-355.
Handbook of Pharmaceutical Excipients, 5th Edition, London, Chicago, Pharmaceutical Press (2006) pp. 21, 93, 96, 100, 211 and 214.
[Marchenko "Technologiya farmacevticheskih preparatov," Odessa (2002) p. 10.] (With relevant English extracts).
[Chueshov "Promyshlennaya tehnologiya lekarstv," Har'kov "Osnova" izdatel'stvo UkrFA] (1999) v. 2, pp. 353-355. (With relevant Engiish extracts).

* cited by examiner

*Primary Examiner* — Brian Gulledge
(74) *Attorney, Agent, or Firm* — Pepper Hamilton LLP

(57) ABSTRACT

The present invention relates to pharmaceutical compositions and, more particularly, to a pharmaceutical composition containing the compound {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol.

19 Claims, No Drawings

PHARMACEUTICAL COMPOSITIONS

CROSS REFERENCE TO RELATED APPLICATIONS

The present application claims priority to U.S. provisional application Ser. No. 60/823,083 filed Aug. 21, 2006, which is incorporated herein by reference in its entirety.

FIELD OF THE INVENTION

The present invention relates to pharmaceutical compositions and, more particularly, to a pharmaceutical composition containing {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol.

BACKGROUND OF THE INVENTION

The compound of formula (I):

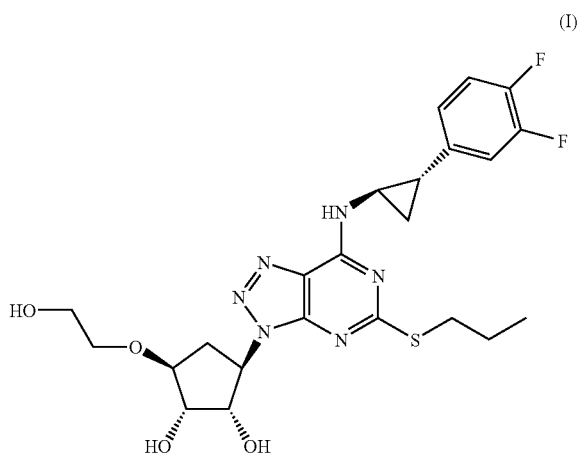 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

is conventionally named {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol, and hereinafter will be referred to as the "Agent."

The Agent is disclosed as an ADP-receptor antagonist in International Patent Application number PCT/SE99/02256 (publication number WO00/34283) and International Patent Application number PCT/SE01/01239 (publication number WO01/92262). It has been found that adenosine 5'-diphosphate (ADP) acts as a key mediator of thrombosis. ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor which is as yet uncloned. The pharmacological characteristics of this receptor have been described, for example, in Humphries et al., Br. J. Pharmacology, 1994, 113, 1057-1063, and Fagura et al., Br. J. Pharmacology, 1998, 124, 157-164. It has been shown that antagonists at this receptor offer significant improvements over other anti-thrombotic agents (see, J. Med. Chem., 1999, 42, 213).

SUMMARY OF THE INVENTION

The present invention provides pharmaceutical compositions comprising: {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol; one or more fillers selected from mannitol, sorbitol, dibasic calcium phosphate dihydrate, dibasic calcium phosphate anhydrate, and tribasic calcium phosphate, or any mixture thereof; one or more binders selected from hydroxypropyl cellulose, alginic acid, carboxymethylcellulose sodium, copovidone, and methylcellulose, or any mixture thereof; one or more disintegrants selected from sodium starch glycolate, croscarmellose sodium, and crospovidone, or any mixture thereof, and one or more lubricants.

In some embodiments, the filler is a mixture of mannitol and dibasic calcium phosphate dihydrate. In any of the foregoing embodiments, the binder is hydroxypropyl cellulose. In any of the foregoing embodiments, the disintegrant is sodium starch glycolate. In any of the foregoing embodiments, the lubricant is magnesium stearate or sodium stearyl fumarate. In any of the foregoing embodiments, {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is present in an amount of 20 to 45% by weight. In any of the foregoing embodiments, the filler is present in an amount of 20 to 70% by weight. In any of the foregoing embodiments, the binder is present in an amount of 3 to 6% by weight. In any of the foregoing embodiments, the disintegrant is present in an amount of 2 to 6% by weight. In any of the foregoing embodiments, the lubricant is present in an amount of 0.5 to 1% by weight. In any of the foregoing embodiments, {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is substantially present in the form of Polymorph II. In any of the foregoing embodiments, {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is substantially present in the form of Polymorph III. In any of the foregoing embodiments, the filler is a mixture of mannitol and dibasic calcium phosphate dehydrate, the binder is hydroxypropyl cellulose, the disintegrant is sodium starch glycolate, and the lubricant is magnesium stearate or sodium stearyl fumarate. In any of the foregoing embodiments, {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is present in an amount of 20 to 45% by weight, mannitol is present in an amount of 20 to 45% by weight, dibasic calcium phosphate dihydrate is present in an amount of 10 to 30% by weight, hydroxypropylcellulose is present in an amount of 3 to 6% by weight, sodium starch glycolate is present in an amount of 2 to 6% by weight, and one or more lubricants is present in an amount of 0.5 to 3% by weight. In any of the foregoing embodiments, the pharmaceutical composition has been prepared by a wet granulation process or a high shear wet granulation process.

DESCRIPTION OF EMBODIMENTS

The pharmaceutical compositions of the present invention are suitable for oral administration. One of the qualities that is desirable in a pharmaceutical composition suitable for oral administration is bioavailability. The bioavailability of a drug is the relative amount of an administered dose that reaches the systemic circulation in an unchanged form. Therefore, bioavailability is important in determining the therapeutically active concentration at the site of action. Both drug release from the formulation and the stability of the formulation will affect its bioavailability. It is therefore important that the drug formulation should release substantially all of the drug (see Aulton Me., Pharmaceutics—The Science of Dosage Form Design, $2^{nd}$ Edition, 2002, Churchill Livingstone). Bioavailability can be measured using tests know in the art such as, for example, using a standard United States Pharmacopoica (USP) dissolution apparatus and a standard 'bio-relevant' dissolution medium such as, for example, FaSSIF (Pharm. Res., 2000, 17, 439-444).

There are pharmaceutical compositions containing the Agent that retain some of the Agent and hence reduce its bioavailability.

We have now discovered a novel pharmaceutical composition of the Agent that has advantageous properties and which solves one or more of the problems associated with formulation of the Agent. In a first aspect, we have discovered a pharmaceutical composition that is suitable for oral administration and that releases substantially all of the Agent. In one aspect, the pharmaceutical composition releases at least 90% of the Agent. In another aspect, the pharmaceutical composition releases at least 95% of the Agent. In yet another aspect, the pharmaceutical composition releases at least 97% of the Agent.

Accordingly, the invention provides a pharmaceutical composition comprising: the Agent; one or more fillers selected from mannitol, sorbitol, dibasic calcium phosphate dihydrate, dibasic calcium phosphate anhydrate, and tribasic calcium phosphate, or any mixture thereof; one or more binders selected from hydroxypropyl cellulose, alginic acid, carboxymethylcellulose sodium, copovidone, and methylcellulose, or any mixture thereof; one or more disintegrants selected from sodium starch glycolate, croscarmellose sodium, and crospovidone, or any mixture thereof, and one or more lubricants.

In one aspect, the pharmaceutical composition contains from 1 to 50% by weight of the Agent. In some embodiments, it contains 20 to 45% by weight of the Agent.

The filler may be a "soluble" filler or an "insoluble" filler. A "soluble" filler is a filler that is substantially soluble in water at ambient temperature. An "insoluble" filler is a filler that has low or slow solubility in water at ambient temperature.

In one aspect, the pharmaceutical composition contains one or more "soluble" fillers. In another aspect, the pharmaceutical composition contains one "soluble" filler. In one aspect, the pharmaceutical composition contains one or more "insoluble" fillers. In another aspect, the pharmaceutical composition contains one "insoluble" filler.

In one aspect, the pharmaceutical composition contains at least one "soluble" filler selected from mannitol, sorbitol, maltodextrin, maltose, and dextrin. In one aspect, the "soluble" filler is mannitol or sorbitol. In another aspect, the "soluble" filler is mannitol.

In another aspect, the pharmaceutical composition contains one or more "insoluble" fillers selected from dibasic calcium phosphate dihydrate, dibasic calcium phosphate anhydrate, partially pre-gelled starch, and tribasic calcium phosphate. In one aspect, the "insoluble" filler is selected from dibasic calcium phosphate dihydrate, dibasic calcium phosphate anhydrate, and tribasic calcium phosphate. In another aspect, the "insoluble" filler is dibasic calcium phosphate dihydrate.

In another aspect, the filler is a mixture of mannitol and dibasic calcium phosphate dihydrate.

In another aspect, the pharmaceutical composition contains from 1 to 90% by weight of filler. In some embodiments, it contains 20 to 70% by weight of filler. In another aspect, the pharmaceutical composition contains from 1 to 70% by weight of "soluble" filler. In some embodiments, it contains 20 to 45% by weight of "soluble" filler. In another aspect, the pharmaceutical composition contains from 1 to 30% by weight of "insoluble" filler. In some embodiments, it contains 10 to 30% by weight of "insoluble" filler.

In one aspect, the pharmaceutical composition contains one or more binders. In another aspect, the pharmaceutical composition contains one binder. In another aspect, the binder is hydroxypropyl cellulose.

In another aspect, the pharmaceutical composition contains from 2 to 8% by weight of binder. In some embodiments, it contains 3 to 6% by weight of binder.

In one aspect, the pharmaceutical composition contains one or more disintegrants. In another aspect, the pharmaceutical composition contains one disintegrant. In one aspect, the disintegrant is sodium starch glycolate or croscarmellose sodium. In one aspect, the disintegrant is sodium starch glycolate.

In another aspect, the pharmaceutical composition contains from 2 to 6% by weight of disintegrant.

In one aspect, the pharmaceutical composition contains one or more lubricants. In another aspect, the pharmaceutical composition contains one lubricant. Suitable lubricants include, for example, magnesium stearate, stearic acid, palmitic acid, calcium stearate, carnauba wax, hydrogenated vegetable oils, mineral oil, polyethylene glycols, and sodium stearyl fumarate. In one aspect, the lubricant is magnesium stearate or sodium stearyl fumarate. In another aspect, the lubricant is magnesium stearate.

Typically, one or more lubricants will be present in an amount 0.5 to 3%, and especially 0.5 to 1% by weight.

Additional conventional excipients, which may be added, include preservatives, stabilisers, anti-oxidants, silica flow conditioners, antiadherents, or glidants.

Other suitable lubricants and additional excipients which may be used are described in Handbook of Pharmaceutical Excipients, $2^{nd}$ Edition, American Pharmaceutical Association; The Theory and Practice of Industrial Pharmacy, 2nd Edition, Lachman, Leon, 1976; Pharmaceutical Dosage Forms: Tablets Volume 1, $2^{nd}$ Edition, Lieberman, Hebert A., et al, 1989; Modern Pharmaceutics, Banker, Gilbert and Rhodes, Christopher T, 1979; and Remington's Pharmaceutical Sciences, $15^{th}$ Edition, 1975.

It will be appreciated that a particular excipient may act as both a binder and a filler, or as a binder, a filler and a disintegrant. Typically, the combined amount of filler, binder, and disintegrant comprises, for example, 50 to 90% by weight of the composition.

In another aspect, the invention relates to a pharmaceutical composition comprising the Agent, mannitol, dibasic calcium phosphate dihydrate, hydroxypropylcellulose, sodium starch glycolate, and one or more lubricants.

In another aspect, the invention relates to a pharmaceutical composition comprising: the Agent in an amount of 20 to 45% by weight; mannitol in an amount of 20 to 45% by weight; dibasic calcium phosphate dihydrate in an amount of 10 to 30% by weight; hydroxypropylcellulose in an amount of 3 to 6% by weight; sodium starch glycolate in an amount of 2 to 6% by weight; and one or more lubricants in an amount of 0.5 to 3% by weight.

It is desirable that the physical properties of these compositions are stable on storage, as changes in for instance, disintegration times, dissolution rates or tablet hardness among others can affect product performance. It is possible that decreases in dissolution rate on storage under International Council for Harmonisation of Technical Requirements for Registration of Pharmaceuticals for Human Use (ICH) stability testing conditions, used to assign product shelf life, can reduce the bioavailability of the Agent. Physical property stability can be measured by USP methodologies for disintegration times and dissolution testing.

It is also desirable that the compositions are chemically stable as degradation by oxidation, hydrolysis, isomerisation, photolysis, polymerization, or any other method of degradation, either as a result of mixing with excipients or by any other method, could lead to a reduction in bioavailability. Chemical stability can be measured by a suitable, stability indicating chromatographic method for determining degradation products (see Aulton Me., Pharmaceutics—The Science of Dosage Form Design, $2^{nd}$ Edition, 2002, Churchill Livingstone).

In another aspect, we have discovered a pharmaceutical composition that is suitable for oral administration that releases substantially all of the Agent and has a desirable stability profile.

In one aspect the invention relates to a pharmaceutical composition prepared by wet granulation. Granulation is a process by which primary particles (powders) are made to adhere to form larger, multiparticulate entities called granules. Granulation normally commences after initial dry mixing of the powdered ingredients so that a fairly uniform distribution of ingredients through the mix is achieved. Granulation methods can be divided into two types, wet granulation methods that utilize a liquid to form the granules and dry methods that do not.

In dry granulation methods, primary powder particles are aggregated under pressure (or compaction). There are two main processes: a large tablet (also known as a slug) is produced with a heavy duty tablet press or the powder particles are compressed between two rollers to produce a sheet or 'ribbon' of material (process known as roller compaction). In both cases, the compacted material is milled using a suitable milling technique to produce granular material. The granules can then be compressed in a standard tablet press to produce tablets.

Wet granulation involves massing the primary powder particles using a granulating fluid. The fluid contains a solvent, which can be removed by drying, and is non-toxic. The granulating fluid can be used alone or more typically with a binding agent (binder) to ensure article adhesion in the dry state. Binding agents can be added to the system as a binder solution (as part of the granulating fluid) or as dry material mixed with the primary powder particles. There are three main types of wet granulator, shear granulators (such as planetary mixers), high shear mixer granulators (such as Fielder or Diosna) and Fluid Bed Granualtors (such as Aeromatic or Glatt).

In another aspect, we have discovered a pharmaceutical composition prepared by a wet granulation process that is suitable for oral administration that releases substantially all of the Agent and a desirable stability profile.

In another aspect, the invention relates to a pharmaceutical composition prepared by a wet granulation process comprising the Agent, mannitol, dibasic calcium phosphate dihydrate, hydroxypropylcellulose, sodium starch glycolate, and one or more lubricants.

In another aspect, the invention relates to a pharmaceutical composition prepared by high shear wet granulation. High shear wet granulation is a process that involves intensive dry mixing of primary powders and subsequent addition of granulating fluid, which results in the formation of granules. The granulating fluid contains a volatile solvent (usually water) and may also include a binder, ensuring particle adhesion (binders may also be added dry as powders to the bulk of the formulation to be granulated). Granules possess major advantages compared to powders, which they are composed of, in terms of improved flow properties, reduced risk of segregation, and increased homogeneity (information taken from Aulton Me., Pharmaceutics—The Science of Dosage Form Design, $2^{nd}$ Edition, 2002, Churchill Livingstone).

In one aspect, the pharmaceutical composition is in a solid dosage form, such as a tablet or capsule. In another aspect, the pharmaceutical composition is in the form of a tablet.

In another aspect the invention relates to a pharmaceutical composition prepared by a high shear wet granulation process comprising the Agent, mannitol, dibasic calcium phosphate dihydrate, hydroxypropylcellulose, sodium starch glycolate, and one or more lubricants.

The Agent exists in an amorphous form and in four different substantially crystalline forms (see International Patent Application number PCT/SE01/01239 (publication number WO01/92262)). In another aspect, the invention relates to a pharmaceutical composition as hereinabove define in which the Agent is in a crystalline form.

In yet another aspect, the invention relates to a pharmaceutical composition comprising the Agent substantially as Polymorph II. In yet another aspect, the invention relates to a pharmaceutical composition comprising the Agent substantially as Polymorph III. In some embodiments, the Agent is at least 90% Polymorph II or Polymorph III. In some embodiments, the Agent is at least 95% Polymorph II or Polymorph III. In some embodiments, the Agent is at least 99% Polymorph II or Polymorph III. In some embodiments, the Agent is at least 99.9% Polymorph II or Polymorph III.

Compositions of the invention, which are of particular interest, include, for example, the specific embodiments set out hereinafter in the accompanying Example. It will be appreciated that modifications of the wet granulation techniques, including the order of addition of the components and their screening and blending prior to compression into tablets, may be carried out according to principles well known in the art.

A further aspect of the present invention comprises a method of preparing a pharmaceutical composition, which comprises admixing the Agent with: one or more fillers selected from mannitol, sorbitol, maltodextrin, maltose, dextrin, dibasic calcium phosphate dihydrate, dibasic calcium phosphate anhydrate, partially pre-gelled starch, and tribasic calcium phosphate, or any mixture thereof; one or more binders selected from hydroxyl propyl cellulose, hydroxyl propyl methylcellulose, alginic acid, carboxymethylcellulose sodium, copovidone, and methylcellulose, or any mixture thereof; one or more disintegrants selected from sodium starch glycolate, croscarmellose sodium, and crospovidone, or any mixture thereof, and one or more lubricants.

The following pharmaceutical composition is intended to illustrate the invention. It should be understood that the example is for illustrative purposes only and is not to be construed as limiting the invention in any manner.

EXAMPLES

Example 1

Pharmaceutical Composition

| Ingredient | Quantity per unit dose Unit dose (mg) | Quantity (% w/w or w/v) |
| --- | --- | --- |
| The Agent | 90.00 | 30.00 |
| Mannitol | 126.00 | 42.00 |
| Dibasic calcium phosphate dihydrate | 63.00 | 21.00 |
| Hydroxypropyl cellulose | 9.00 | 3.00 |
| Sodium starch glycolate | 9.00 | 3.00 |
| Magnesium stearate | 3.00 | 1.00 |
| Core tablet weight | 300.000 | 100.00 |

A high shear wet granulator (Fielder GP1 with 10 L bowl) was used to dry mix the Agent, mannitol, dibasic calcium phosphate dihydrate, hydroxypropyl cellulose, and sodium starch glycolate in amounts to give 2.5 kg of total formulation, for 4 minutes. Water was added via a pressure pot at approximately 50 g/minute to approximately 25% w/w. The total mixing time was approximately 10 minutes.

The fluid bed was dried using a Glatt GPCG1 at 60° C. to a product temperature of 42° C. The resulting granule was milled by Quadro Comil 197. The milled granules were blended with magnesium stearate and tablets were compressed from the blend.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:

1. A pharmaceutical composition comprising:
   {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol as the active ingredient;
   and further comprising:
   a filler consisting essentially of a mixture of mannitol and dibasic calcium phosphate dihydrate;
   a binder consisting essentially of hydroxypropyl cellulose;
   a disintegrant consisting essentially of sodium starch glycolate; and
   one or more lubricants.

2. A pharmaceutical composition according to claim 1 wherein the lubricant is magnesium stearate or sodium stearyl fumarate.

3. A pharmaceutical composition according to claim 1 wherein {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is present in an amount of 20 to 45% by weight of the pharmaceutical composition as a whole.

4. A pharmaceutical composition according to claim 1 wherein the filler is present in an amount of 20 to 70% by weight of the pharmaceutical composition as a whole.

5. A pharmaceutical composition according to claim 1 wherein the binder is present in an amount of 3 to 6% by weight of the pharmaceutical composition as a whole.

6. A pharmaceutical composition according to claim 1 wherein the disintegrant is present in an amount of 2 to 6% by weight of the pharmaceutical composition as a whole.

7. A pharmaceutical composition according to claim 1 wherein the lubricant is present in an amount of 0.5 to 1% by weight of the pharmaceutical composition as a whole.

8. A pharmaceutical composition according to claim 1 wherein {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is substantially present in the form of Polymorph II.

9. A pharmaceutical composition according to claim 1 wherein {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol is substantially present in the form of Polymorph III.

10. A pharmaceutical composition according to claim 1 wherein:
    the lubricant is magnesium stearate.

11. A pharmaceutical composition according to claim 1 comprising:
    {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol in an amount of 20 to 45% by weight of the pharmaceutical composition as a whole;
    mannitol in an amount of 20 to 45% by weight of the pharmaceutical composition as a whole;
    dibasic calcium phosphate dihydrate in an amount of 10 to 30% by weight of the pharmaceutical composition as a whole;
    hydroxypropylcellulose in an amount of 3 to 6% by weight of the pharmaceutical composition as a whole;
    sodium starch glycolate in an amount of 2 to 6% by weight of the pharmaceutical composition as a whole; and
    lubricant in an amount of 0.5 to 3% by weight of the pharmaceutical composition as a whole.

12. A pharmaceutical composition according to claim 1 which has been prepared by a wet granulation process.

13. A pharmaceutical composition according to claim 1 which has been prepared by a high shear wet granulation process.

14. A pharmaceutical composition according to claim 1 wherein the combined amount of filler, binder, and disintegrant is 50 to 90% by weight of the pharmaceutical composition as a whole.

15. A pharmaceutical composition according to claim 1 wherein the active ingredient is admixed with filler, binder, disintegrant, and one or more lubricants.

16. A pharmaceutical composition according to claim 1 wherein the composition is a tablet.

17. A pharmaceutical composition according to claim 1 wherein the composition is a core tablet.

18. An oral immediate release pharmaceutical composition comprising:
    {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol substantially present in the form of Polymorph II in an amount of 20 to 45% by weight of the pharmaceutical composition as a whole;

mannitol in an amount of 20 to 45% by weight of the pharmaceutical composition as a whole;

dibasic calcium phosphate dihydrate in an amount of 10 to 30% by weight of the pharmaceutical composition as a whole;

hydroxypropyl cellulose in an amount of 3 to 6% by weight of the pharmaceutical composition as a whole;

sodium starch glycolate in an amount of 2 to 6% by weight of the pharmaceutical composition as a whole; and one or more lubricants in an amount of 0.5 to 3% by weight of the pharmaceutical composition as a whole.

19. An oral pharmaceutical composition consisting of:

{1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol substantially present in the form of Polymorph II in an amount of 20 to 45% by weight of the pharmaceutical composition as a whole;

mannitol in an amount of 20 to 45% by weight of the pharmaceutical composition as a whole;

dibasic calcium phosphate dihydrate in an amount of 10 to 30% by weight of the pharmaceutical composition as a whole;

hydroxypropyl cellulose in an amount of 3 to 6% by weight of the pharmaceutical composition as a whole;

sodium starch glycolate in an amount of 2 to 6% by weight of the pharmaceutical composition as a whole; and one or more lubricants in an amount of 0.5 to 3% by weight of the pharmaceutical composition as a whole.

* * * * *

UNITED STATES PATENT AND TRADEMARK OFFICE
CERTIFICATE OF CORRECTION

PATENT NO.       : 8,425,934 B2
APPLICATION NO.  : 11/841030
DATED            : April 23, 2013
INVENTOR(S)      : Simon Banks Page 1 of 1

It is certified that error appears in the above-identified patent and that said Letters Patent is hereby corrected as shown below:

In the Claims

At Column 8, Line 62 (Claim 18), An oral "immediate release" pharmaceutical composition comprising: should read --An oral pharmaceutical composition comprising:--

Signed and Sealed this
Twenty-fifth Day of June, 2013

Teresa Stanek Rea
*Acting Director of the United States Patent and Trademark Office*